(12) United States Patent
Jang et al.

(10) Patent No.: US 11,925,478 B2
(45) Date of Patent: Mar. 12, 2024

(54) IMPLANTABLE BIOSENSOR

(71) Applicant: Daegu Gyeongbuk Institute of Science and Technology, Daegu (KR)

(72) Inventors: Kyung In Jang, Incheon (KR); Jong Cheol Rah, Daegu (KR); Han Hee Jung, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 482 days.

(21) Appl. No.: 16/793,775

(22) Filed: Feb. 18, 2020

(65) Prior Publication Data
US 2021/0137456 A1 May 13, 2021

(30) Foreign Application Priority Data
Nov. 8, 2019 (KR) .......................... 10-2019-0142337

(51) Int. Cl.
*A61B 5/00* (2006.01)
*B82Y 30/00* (2011.01)

(52) U.S. Cl.
CPC ...... *A61B 5/686* (2013.01); *A61B 2562/0295* (2013.01); *A61B 2562/18* (2013.01); *B82Y 30/00* (2013.01)

(58) Field of Classification Search
CPC ............ A61B 5/686; A61B 2562/0295; A61B 2562/18; B82Y 30/00
See application file for complete search history.

(56) References Cited

U.S. PATENT DOCUMENTS

2004/0058433 A1* 3/2004 Yu ...................... G01N 33/5438
435/287.2
2011/0042225 A1 2/2011 Adeloju

FOREIGN PATENT DOCUMENTS

| CN | 108695403 A | * 10/2018 | |
|---|---|---|---|
| JP | 2019-170701 | 10/2019 | |
| KR | 10-2013-0057477 | 5/2013 | |
| WO | WO-2009102077 A1 | * 8/2009 | ............ H05K 1/095 |
| WO | 2012-045425 | 4/2012 | |

OTHER PUBLICATIONS

ESpacenet Translation of JP2019170701A used in Non-Final Rejection, (Year: 2019).*
ESpacenet Translation of KR20130057477A used in Non-Final Rejection, (Year: 2013).*
Lu Cao et al., "Facile and inexpensive fabrication of zinc oxide based bio-surfaces for C-reactive protein detection", Sci Rep 8, 12687, Aug. 23, 2018.
KIPO, Office Action of KR 10-2019-0142337 dated Feb. 25, 2021.

* cited by examiner

*Primary Examiner* — Patrick Fernandes
(74) *Attorney, Agent, or Firm* — LEX IP MEISTER, PLLC

(57) ABSTRACT

Provided is an implantable biosensor including an intermediate layer; a first electrode layer provided on one surface of the intermediate layer and including a first electrode configured to react with a bio material and an auxiliary electrode electrically connected to the first electrode; and a second electrode layer provided on another surface of the intermediate layer to face the first electrode layer and including a second electrode operating as a reference electrode.

7 Claims, 7 Drawing Sheets

(a)　　　　　　(b)　　　　　　(c)

IMPLANTABLE BIOSENSOR

CROSS-REFERENCE TO RELATED APPLICATION

This application claims the benefit of Korean Patent Application No. 10-2019-0142337, filed on Nov. 8, 2019, in the Korean Intellectual Property Office, the disclosure of which is incorporated herein in its entirety by reference.

BACKGROUND

1. Field

One or more embodiments relate to an implantable biosensor.

2. Description of Related Art

In the case of conventional biosensors provided outside a living body, experiments have been conducted with regard to electrodes installed in electrochemical cells. Such biosensors are not suitable for insertion into a living body because of their large size and hard material. Also, although a needle-type biosensor has been developed as a probe-type biosensor, such biosensor is still made of a hard material, which causes skin and body irritation and damages to the interior of a living body. Therefore, it is difficult to use such a biosensor for a long time. Also, in the case of a conventional biosensor that employs a three-electrode system including a working electrode, a reference electrode, and a counter electrode to sense a bio material and measure the concentration thereof, each electrode needs to be individually inserted into a living body, and thus damages to the interior of the living body may occur.

The above-described related art is technical information possessed by the inventor for derivation of the present disclosure or acquired during the process of deriving the present disclosure and may not necessarily be known technology disclosed to the general public before the application of the present disclosure.

SUMMARY

One or more embodiments provide an implantable biosensor that may significantly reduce damages to the interior of the living body.

Additional aspects will be set forth in part in the description which follows and, in part, will be apparent from the description, or may be learned by practice of the presented embodiments of the disclosure.

According to one or more embodiments, an implantable biosensor includes an intermediate layer; a first electrode layer provided on one surface of the intermediate layer and including a first electrode configured to react with a bio material and an auxiliary electrode electrically connected to the first electrode; and a second electrode layer provided on another surface of the intermediate layer to face the first electrode layer and including a second electrode operating as a reference electrode.

The first electrode may include a first electrode end provided at a leading end; and a first leading wire extending from the first electrode end, connected to the outside, curved in one direction, and stretchable in the one direction.

The auxiliary electrode may include an auxiliary electrode end provided at a leading end; and an auxiliary leading wire extending from the auxiliary electrode end, connected to the outside, curved in one direction, and stretchable in the one direction.

The first electrode may further include a sensing unit provided at a leading end of the first electrode and configured to sense the bio material.

The sensing unit may include a support ring having an annular shape, provided on one surface of the first electrode, and having an internal space; a fixing material provided in the internal space of the support ring; and a sensing material provided on a top surface of the fixing material and reacting with the bio material.

The sensing material may be an enzyme, and the isoelectric point of the fixing material may be higher than the isoelectric point of the sensing material.

The fixing material may be zinc oxide nano-rods, and the sensing material may be tyrosinase.

The second electrode may include a second electrode end provided at a leading end; and a second leading wire extending from the second electrode end, connected to the outside, curved in one direction, and stretchable in the one direction.

The second electrode may further include a metal paste provided on one side of the second electrode.

The implantable biosensor may further include a protective layer entirely covering the intermediate layer, the first electrode layer, and the second electrode layer, wherein the intermediate layer and the protective layer may each include a flexible biocompatible polymer.

Other aspects, features, and advantages will become apparent from the following drawings, claims, and detailed description of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
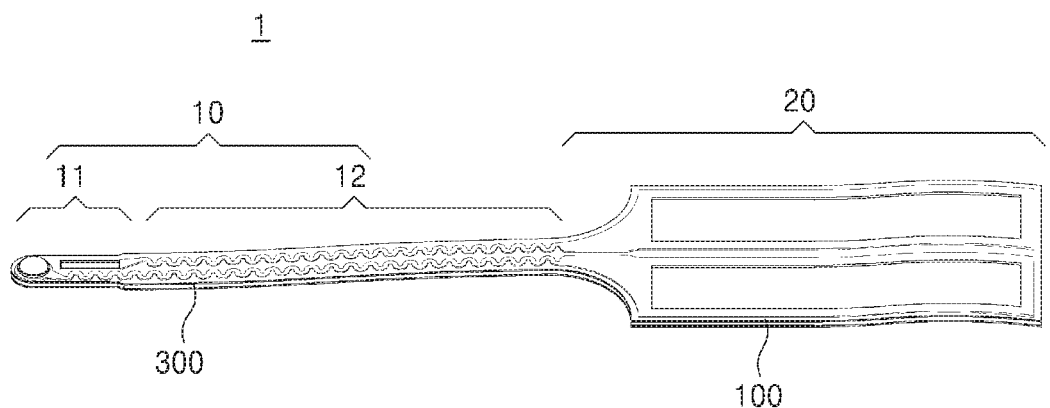
FIGS. 1A and 1B are diagrams showing an implantable biosensor according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

While such terms as "first," "second," etc., may be used to describe various elements, such elements must not be limited to the above terms. The above terms may be used only to distinguish one element from another.

The terms used in the present specification are merely used to describe particular embodiments, and are not intended to limit the disclosure. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, with reference the accompanying drawings, one or more embodiments will be described in detail. In the present specification, the lengthwise direction, the widthwise direction, and the heightwise direction may respectively correspond to the front-rear direction, the left-right direction, and the vertical direction. In addition, the lengthwise direction, the widthwise direction, and the heightwise direction may correspond to the X-axis direction, the Y-axis direction, and the Z-axis direction, respectively.

Figure 1B:
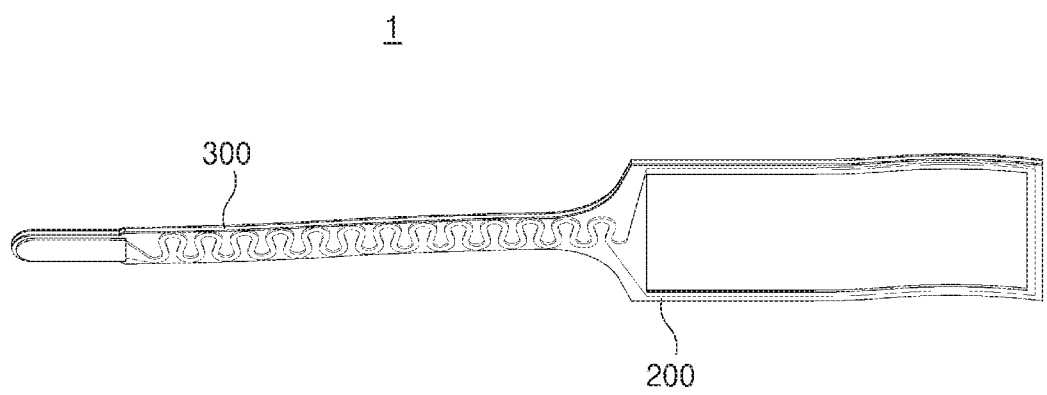
Figure 2:
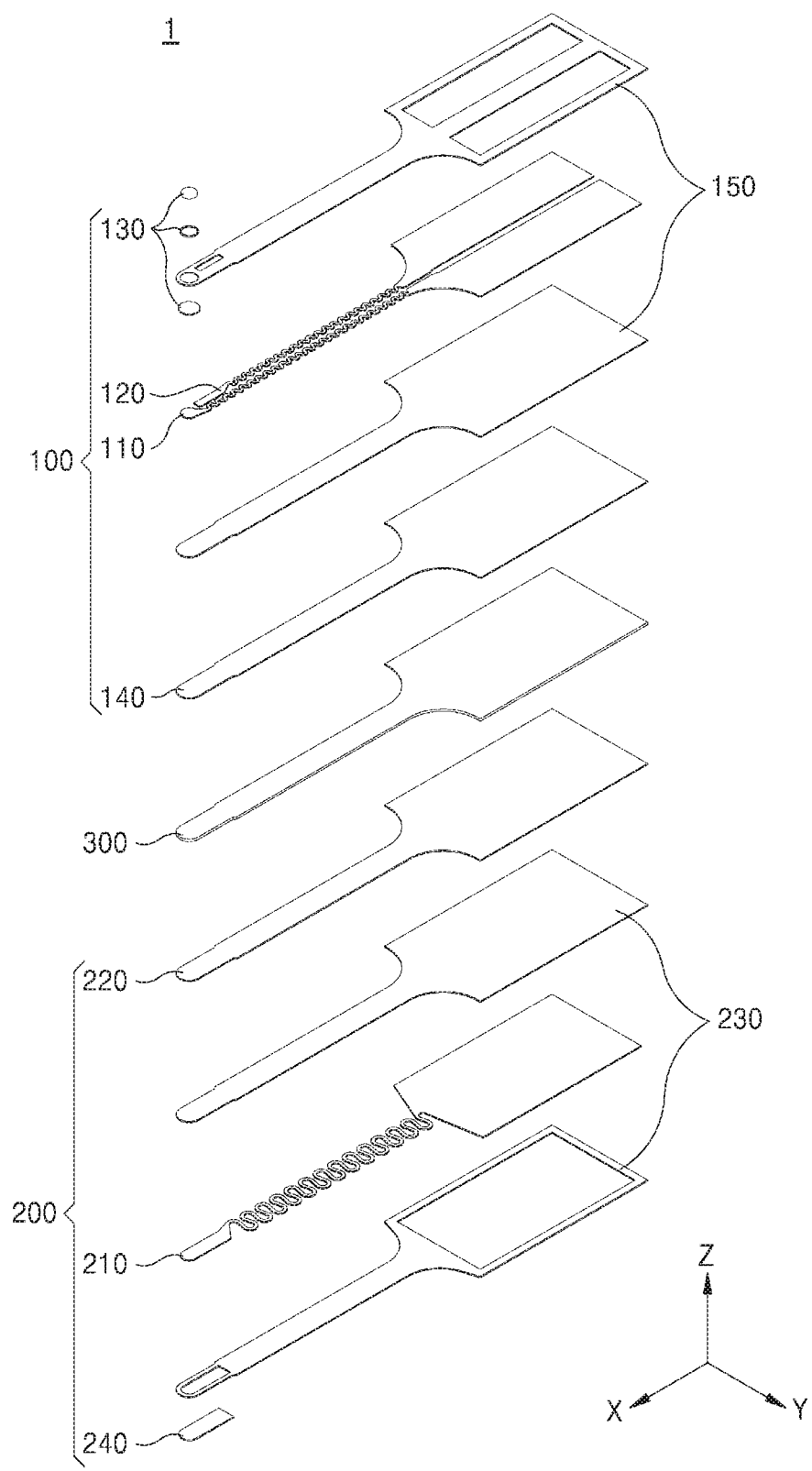
FIG. 2 is an exploded perspective view of the implantable biosensor of FIG. 1.

FIG. 1 is a diagram showing an implantable biosensor 1 according to an embodiment. In detail, FIG. 1A is a perspective view of the implantable biosensor 1 viewed in one direction, and FIG. 1B is a perspective view of the implantable biosensor 1 viewed in another direction. FIG. 2 is an exploded perspective view of the implantable biosensor 1 of FIG. 1.

Referring to FIGS. 1 and 2, the implantable biosensor 1 according to an embodiment includes a first electrode layer 100, which includes a first electrode 110 and an auxiliary electrode 120, a second electrode layer 200, which includes a second electrode 210 and is arranged to face the first electrode layer 100, and an intermediate layer 300, which is interposed between the first electrode layer 100 and the second electrode layer 200 and interconnects the first electrode layer 100 and the second electrode layer 200.

As shown in FIGS. 1 and 2, the implantable biosensor 1 according to one or more embodiments may include a probe unit 10 and a pad unit 20. The probe unit 10 is a portion to be inserted into a living body and has a probe-like shape extending in one direction (e.g., the X-axis direction of FIG. 2). The length of the probe unit 10 may be appropriately selected according to a portion of a living body to which the implantable biosensor is to be inserted and the type of a target material to be sensed.

The probe unit 10 may include a sensor 11 and a connector 12. The sensor 11 is located at the leading end of the probe unit 10, that is, the leading end of the implantable biosensor 1. The sensor 11 may include a first electrode end 111 of the first electrode 110, an auxiliary electrode end 121 of the auxiliary electrode 120, and a sensing unit 130 that are to be described below. When a potential is applied to the implantable biosensor 1 by an external electronic device while the implantable biosensor 1 is being inserted into a living body, a redox reaction of a bio material may occur at the sensor 11. Here, the bio material includes neural materials or biochemical ions. Also, the external electronic device is not limited to particular electronic devices and may be an electronic device commonly used in electrochemical experiments. For example, the external electronic device may include a voltmeter, an ammeter, a potentiostat, a PC, etc.

The connector 12 extends in one direction from the probe unit 10 and interconnects the probe unit 10 and the pad unit 20. In the connector 12, a first leading wire 112 of the first electrode 110, an auxiliary leading wire 122 of the auxiliary electrode 120, and a second leading wire 212 of the second electrode 210, which are described below, may be provided. When a redox reaction of a bio material occurs in the sensor 11, charges generated therefrom are transferred to the pad unit 20, and a current value may be measured through an external electronic device. Accordingly, the concentration of a particular material present in a living body may be measured.

The width (e.g., the length in the Y-axis direction of FIG. 2) of the connector 12 may be greater than the width of the sensor 11. Also, as shown in FIG. 1, a portion where the sensor 11 and the connector 12 are connected to each other may have a tapered shape. However, the shape of the portion where the sensor 11 and the connector 12 are connected to each other is not limited to the above. Thus, the portion where the sensor 11 and the connector 12 are connected are connected to each other may have a rounded shape that is convex outward. According to this configuration, the probe unit 10 may be more smoothly inserted into a living body, thereby minimizing damage to the living body.

The pad unit 20 is arranged outside a living body when the implantable biosensor 1 is used. The pad unit 20 is connected to an external electronic device and has a larger area than the probe unit 10. According to one embodiment, the pad unit 20 may have a flat plate shape. Also, as shown in FIG. 1, the pad unit 20 may have a tapered shape with a cross-sectional area that becomes narrower toward the probe unit 10. In some cases, a tapered portion of the pad unit 20 may also be inserted into the living body together with the probe unit 10.

The pad unit 20 is connected to an external electronic device. Therefore, a constant voltage may be applied to the sensor 11, and a bio material may react with the sensor 11. Such a reaction may be a redox reaction, and, by measuring the amount of charges generated or consumed by the reaction in real time through an external electronic device, the presence of a bio material may be sensed and the concentration thereof may be measured.

The implantable biosensor 1 according to one or more embodiments has flexible and stretchable characteristics, and thus impact applied to the implantable biosensor 1 during the process of being inserted into the living body may be reduced. Also, the implantable biosensor 1 according to one or more embodiments may reduce a difference of mechanical strengths with the internal tissue of the living body, thereby reducing the feeling of irritation and reducing damage to the interior of the living body.

In another embodiment, as described below, the implantable biosensor 1 according to one or more embodiments is covered by a flexible and stretchable protective layer, which further ensures the elasticity and flexibility of the implantable biosensor 1.

Figure 3:
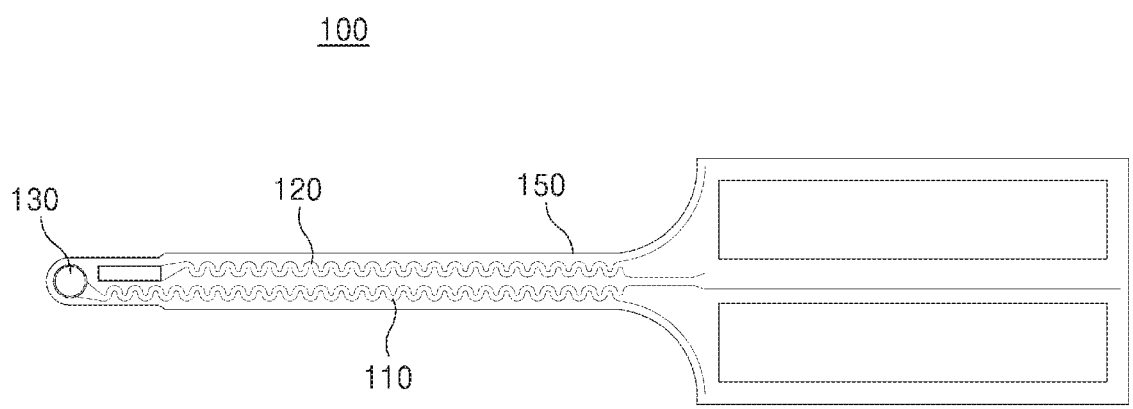
FIG. 3 is a plan view of a first electrode layer of FIG. 2.
Figure 4:
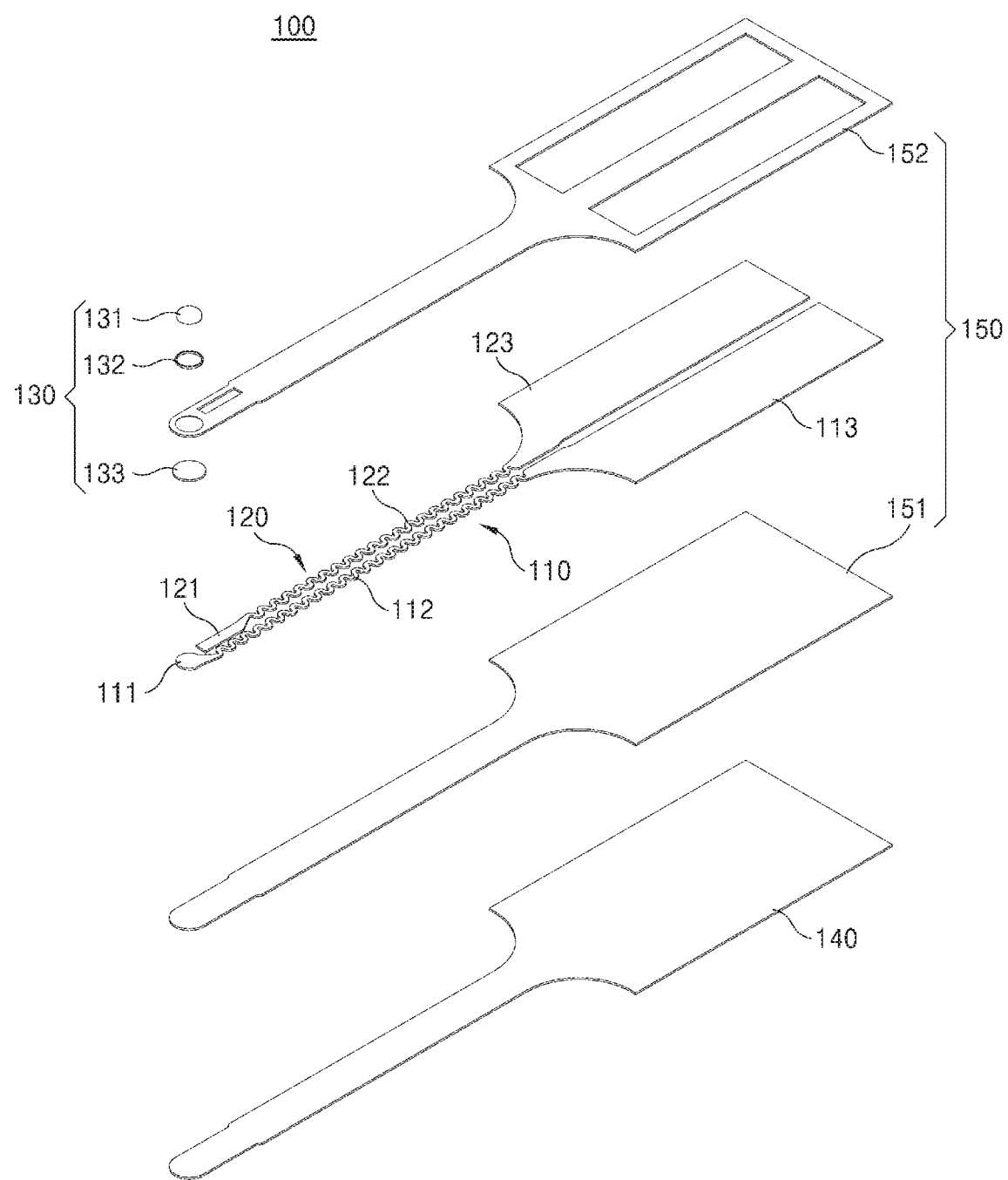
FIG. 4 is an exploded perspective view of the first electrode layer of FIG. 3.
Figure 5:
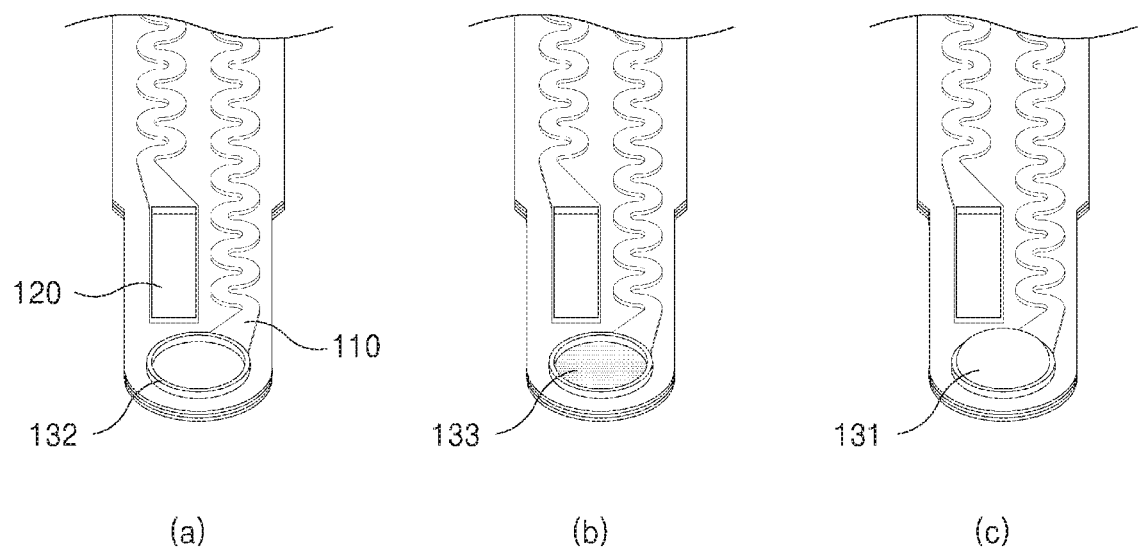
FIG. 5 is a diagram showing a sensing unit of FIG. 3.

FIG. 3 is a plan view of the first electrode layer 100 of FIG. 2. FIG. 4 is an exploded perspective view of the first electrode layer 100 of FIG. 3. FIG. 5 is a diagram showing the sensing unit 130 of FIG. 3 in detail.

Referring to FIGS. 1 to 5, the first electrode layer 100 according to one or more embodiments is provided on one surface of the implantable biosensor 1. The first electrode layer 100 includes a portion to be inserted into the living body and a portion connected to an external electronic device to correspond to the shapes of the probe unit 10 and the pad unit 20 of the implantable biosensor 1 described above. The first electrode layer 100 may include the first electrode 110, the auxiliary electrode 120, the sensing unit 130, a first coupling layer 140, and a first protective layer 150.

The first electrode 110 is an electrode in which a reaction of a bio material occurs. For example, the first electrode 110 may be a working electrode of a three electrode system. Also, the first electrode 110 may be an electrode in which an oxidation reaction or a reduction reaction of a bio material occurs. The first electrode 110 may include a first electrode end 111, a first leading wire 112, and a first pad 113.

The first electrode end 111 is located at the leading end of the first electrode 110 in one direction (e.g., the X-axis direction of FIG. 2). The first electrode end 111 may be located in the sensor 11 of the probe unit 10 and may be inserted into the living body. In one or more embodiments, the first electrode end 111 may supply a reduction current received from the pad unit 20 connected to an external electronic device. Therefore, the implantable biosensor 1 may measure a reduction current generated while a bio material is reduced at the first electrode end 111. The shape of the first electrode end 111 is not particularly limited, and, in one or more embodiments, the leading end portion of the first electrode end 111 may be convex in one direction. The size of the first electrode end 111 is not particularly limited and may have a size corresponding to the size of the sensing unit 130 described below.

The first leading wire 112 extends in one direction from the first electrode end 111 and is connected to an external device. In detail, the first leading wire 112 physically and electrically connects the first electrode end 111 and the first pad 113. The first leading wire 112 may be located in the connector 12 of the probe unit 10 and inserted into the living body. The first leading wire 112 may have the shape of a ribbon that is curved in the lengthwise direction. Therefore, even when the implantable biosensor 1 is contracted, extended, or bent in the lengthwise direction while being inserted into the living body, deformation or damage of the entire implantable biosensor 1 may be minimized. Also, even when the implantable biosensor 1 collides with a living tissue during the process of being inserted into the living body, the impact applied to the implantable biosensor 1 may be reduced. Also, the elasticity of the implantable biosensor 1 in the lengthwise direction may be further improved.

The first pad 113 extends rearward from the first leading wire 112. The first pad 113 may be located in the pad unit 20 and may be connected to an external electronic device. The size and the shape of the first pad 113 are not particularly limited, but the first pad 113 may have an area larger than the first electrode end 111 and the first leading wire 112. In one or more embodiments, the first pad 113 may have the shape of a flat plate narrowed toward the first leading wire 112.

The first electrode end 111, the first leading wire 112, and the first pad 113 may all be arranged on the same plane. Also, the first electrode end 111, the first leading wire 112, and the first pad 113 may all include platinum (Pt). However, one or more embodiments are not limited thereto, and a different material may be partially employed in consideration of a bio material to be measured. For example, the first electrode 110 may include gold (Au), mercury (Hg), carbon (C), etc.

The auxiliary electrode 120 is an electrode which is electrically connected with the first electrode 110. For example, the auxiliary electrode 120 may be a counter electrode of a three electrode system. The auxiliary electrode 120 may be provided on the same plane as the first electrode 110 and may be apart from the first electrode 110. The auxiliary electrode 120 may include an auxiliary electrode end 121, an auxiliary leading wire 122, and an auxiliary pad 123.

The auxiliary electrode end 121 is located at the leading end of the auxiliary electrode 120 in one direction (e.g., the X-axis direction of FIG. 2). The auxiliary electrode end 121 may be located in the sensor 11 of the probe unit 10 and may be inserted into the living body. The shape of the auxiliary electrode end 121 is not particularly limited and may have the shape of a rectangular flat plate in one or more embodiments. Also, in one or more embodiments, the auxiliary electrode end 121 may be provided behind the first electrode end 111. The size of the first electrode end 111 is not particularly limited and may be appropriately selected according to a bio material to be measured.

The auxiliary leading wire 112 extends in one direction from the auxiliary electrode end 121 and is connected to an external device. In detail, the auxiliary leading wire 122 physically and electrically connects the auxiliary electrode end 121 and the auxiliary pad 123. The auxiliary leading wire 122 may be located in the connector 12 of the probe unit 10 and inserted into the living body. The auxiliary leading wire 122 may have the shape of a ribbon that is curved in the lengthwise direction. Therefore, even when the implantable biosensor 1 is contracted, extended, or bent in the lengthwise direction while being inserted into the living body, deformation or damage of the entire implantable biosensor 1 may be minimized. Also, even when the implantable biosensor 1 collides with a living tissue during the process of being inserted into the living body, the impact applied to the implantable biosensor 1 may be reduced. Also, the elasticity of the implantable biosensor 1 in the lengthwise direction may be further improved.

The auxiliary pad 123 extends rearward from the auxiliary leading wire 122. The auxiliary pad 113 may be located in the pad unit 20 and may be connected to an external electronic device. The size and the shape of the auxiliary pad 123 are not particularly limited, but the auxiliary pad 123 may have an area larger than the auxiliary electrode end 121 and the auxiliary leading wire 122. In one or more embodiments, the auxiliary pad 123 may have the shape of a flat plate narrowed toward the auxiliary leading wire 122.

The auxiliary electrode end 121, the auxiliary leading wire 122, and the auxiliary pad 123 may all be arranged on the same plane. Also, the auxiliary electrode end 121, the auxiliary leading wire 122, and the auxiliary pad 123 may all include Pt. However, one or more embodiments are not limited thereto, and a different material may be partially employed in consideration of a bio material to be measured. For example, the auxiliary electrode 120 may include Au, C, nickel (Ni), etc.

In one or more embodiments, it is shown that the first electrode 110 and the auxiliary electrode 120 have almost the same area, but one or more embodiments are not limited thereto. For example, the auxiliary electrode 120 may have a larger area than the first electrode 110. As a result, a current density in the auxiliary electrode 120 is reduced, thereby preventing the overvoltage of the auxiliary electrode 120 from increasing.

Also, the first electrode 110 and the auxiliary electrode 120 are thin-film type electrodes exhibiting excellent elasticity and flexibility, and thus the first electrode 110 and the auxiliary electrode 120 may be naturally curved as forces are applied in three-axis directions.

The sensing unit 130 directly reacts with a bio material to induce a redox reaction of the bio material. Referring to FIGS. 3 to 5, the sensing unit 130 may be provided on the first electrode end 111 of the first electrode 110. The sensing unit 130 may include a sensing material 131, a support ring 132, and a fixing material 133.

The sensing material 131 may be provided on the first electrode end 111. The sensing material 131 reacts with the bio material, such that the bio material is oxidized or reduced at the first electrode 110 of the implantable biosensor 1. For example, the sensing material 131 may oxidize the bio material, and the oxidized bio material may be reduced at the first electrode end 111. By measuring the amount of charges generated or consumed during the process by using an external electronic device connected to the pad unit 20, the bio material may be sensed and the concentration thereof may be measured. In detail, the sensing material 131 may be an enzyme. More particularly, the sensing material 131 may be tyrosinase.

Tyrosinase causes an oxidation reaction with dopamine, and thus dopamine turns into DA quinone. The DA quinone produced as described above is reduced at the first electrode end 111 and becomes dopamine again. The implantable biosensor 1 according to one or more embodiments may be connected to an external electronic device and measure the concentration of dopamine by measuring the amount of charges generated or consumed during the process. In other words, the implantable biosensor 1 according to one or more embodiments may be a sensor for measuring the concentration of dopamine. However, one or more embodiments are not limited thereto, and various types of sensing materials 131 may be used according to bio materials to be sensed.

Referring to FIGS. 4 and 5, the support ring 132 may be provided on the first electrode end 111. The support ring 132 is an annular member having an internal space in which the sensing material 131 may be provided. To this end, the support ring 132 may protrude to have a predetermined height. The sensing material 131 may be fixed to the internal space of the support ring 132. Also, during the process of arranging the sensing material 131 on the first electrode end 111, the support material 132 protruding in the heightwise direction may prevent the sensing material 131 from being arranged on a member other than the first electrode 110 (e.g., the auxiliary electrode 120).

Referring to FIGS. 4 and 5, the fixing material 133 may be provided between the first electrode end 111 and the sensing material 131. The fixing material 133 is a material provided on the first electrode end 111 to fix the sensing material 131 to the first electrode end 111. In one or more embodiments, the fixing material 133 may be zinc oxide (ZnO). More particularly, the fixing material 133 may be zinc oxide nano-rods.

As described above, when tyrosinase is used as the sensing material 131, the isoelectric point (IEP) of zinc oxide nano-rods is pH 9.5, which is higher than the IEP of tyrosinase (pH 6.95). Therefore, zinc oxide nano-rods may more strongly adsorb and fix tyrosinase.

Also, zinc oxide nano-rods have a high direct band gap. Therefore, charges generated when dopamine is oxidized by tyrosinase and is changed into DA quinone may be prevented from being directly absorbed by the first electrode 110. Also, zinc oxide nano-rods supply a reduction current to DA quinone and may measure a reduction current generated when the DA quinone is changed back to dopamine. Accordingly, the implantable biosensor 1 according to one or more embodiments may accurately measure the concentration of dopamine.

Referring to FIGS. 3 and 4, the first electrode layer 100 may further include a first coupling layer 140. The first coupling layer 140 is provided below the first electrode layer 100 and couples the first electrode layer 100 with the intermediate layer 300 described below. The size and the shape of the first coupling layer 140 may correspond to the sizes and the shapes of the first electrode 110 and the auxiliary electrode 120. The material constituting the first coupling layer 140 is not particularly limited, and, in one or more embodiments, the material constituting the first coupling layer 140 may be $SiO_2$. Also, the first coupling layer 140 may have a shape corresponding to the shapes of the probe unit 10 and the pad unit 20 described above.

Also, referring to FIGS. 3 and 4, the first electrode layer 100 may further include a first protective layer 150. The first protective layer 150 may be provided on one surface of the first coupling layer 140 and may cover the first electrode 110 and the auxiliary electrode 120. The material constituting the first protective layer 150 is not particularly limited, and, in one or more embodiments, the material constituting the first protective layer 150 may be PDMS or polyimide (PI).

The first protective layer 150 may include a protective layer 1a 151 covering bottom surfaces of the first electrode 110 and the auxiliary electrode 120 and a protective layer 1b 152 covering top surfaces of the first electrode 110 and the auxiliary electrode 120. The protective layer 1a 151 is provided on the top surface of the first coupling layer 140 and has a shape and a size similar to those of the first coupling layer 140. The protective layer 1b 152 is provided on the top surfaces of the first electrode 110 and the auxiliary electrode 120, wherein protective layer 1b 152 is partially cut.

In detail, portions of the protective layer 1b 152 corresponding to the first electrode end 111, the first pad 113, the auxiliary electrode end 121, and the auxiliary pad 123 may be cut. Therefore, one surface of each of the first electrode end 111, the first pad 113, the auxiliary electrode end 121, and the auxiliary pad 123 may be exposed. Also, the sensing unit 130 may be provided on an exposed portion of the first electrode end 111. Also, since the auxiliary electrode end 121 is exposed, the auxiliary electrode 120 may constitute an electric circuit together with the first electrode 110. Also, the first pad 113 and the auxiliary pad 123 may be connected to an external electronic device. The first leading wire 112 and the auxiliary leading wire 122 may be covered by the first protective layer 150. The areas of the protective layer 1a 151 and the protective layer 1b 152 may be larger than the areas of the first electrode 110 and the auxiliary electrode 120. Therefore, as the protective layer 1a 151 and the protective layer 1b 152 contact each other, side surfaces of the first electrode 110 and the auxiliary electrode 120 may not be exposed to the outside.

According to the configuration as described above, the first electrode 110 and the auxiliary electrode 120 are entirely covered by the first protective layer 150, thereby reducing the impact applied to the implantable biosensor 1 when the implantable biosensor 1 is inserted into the living body. Also, the overall elasticity and flexibility of the implantable biosensor 1 may be further improved.

Figure 6:
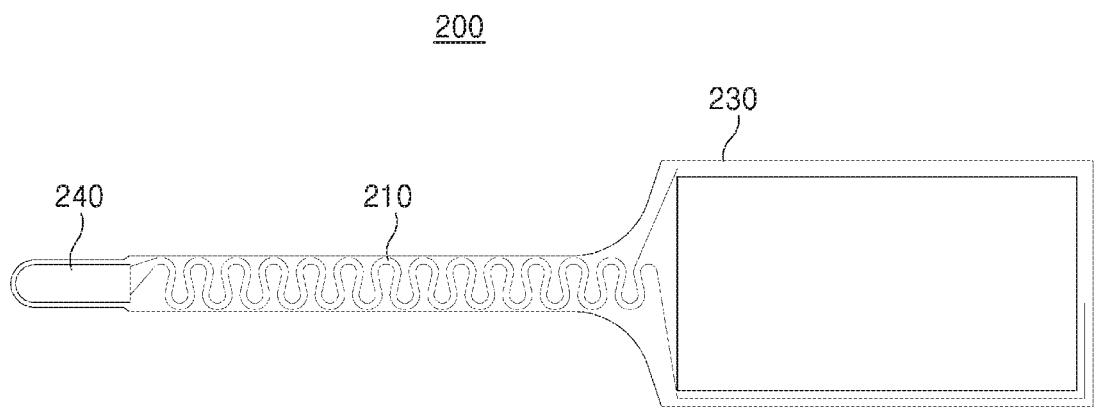
FIG. 6 is a plan view of a second electrode layer of FIG. 1.
Figure 7:
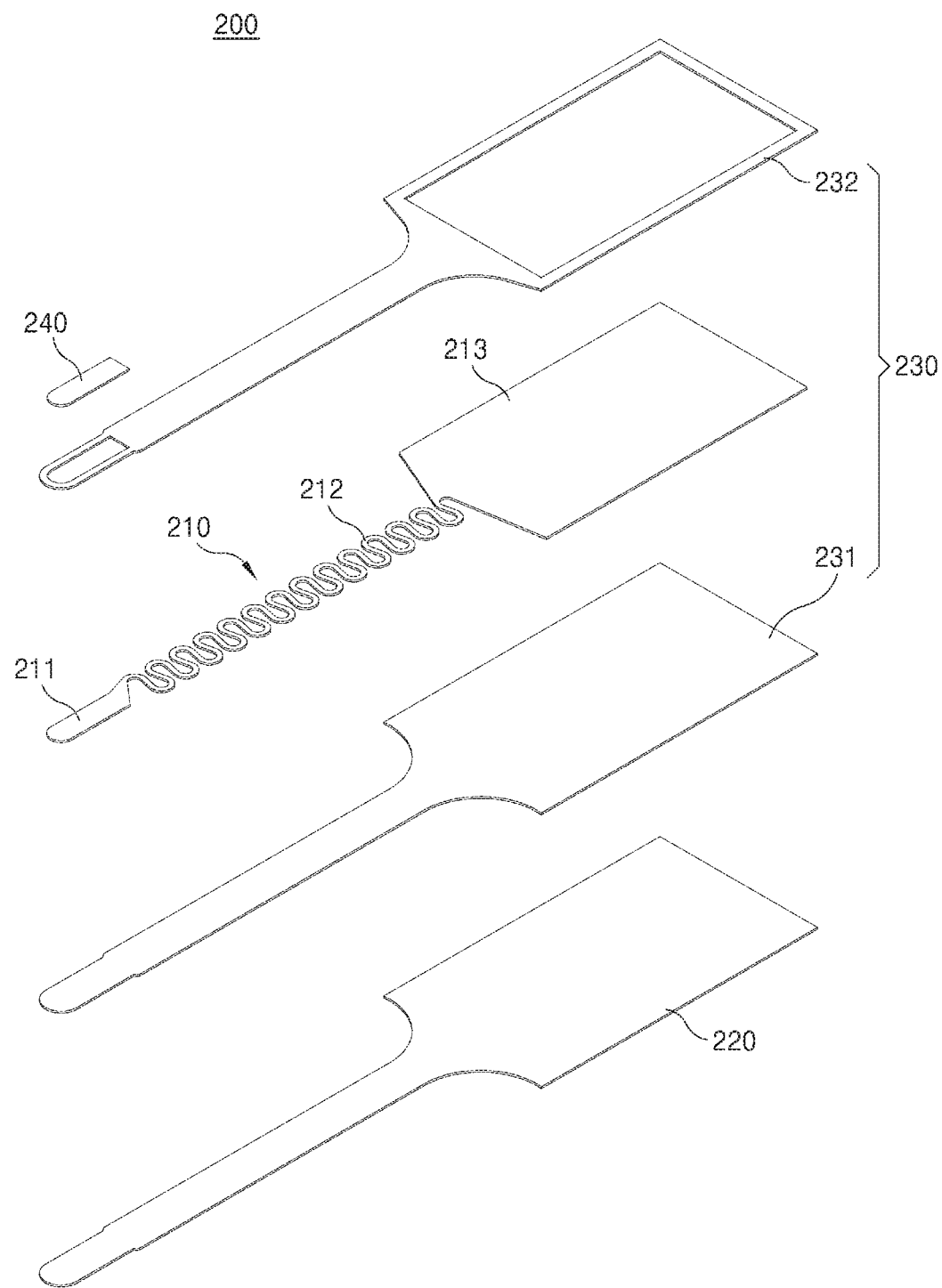
FIG. 7 is an exploded perspective view of the second electrode layer of FIG. 6.

FIG. 6 is a plan view of the second electrode layer 200 of FIG. 1. FIG. 7 is an exploded perspective view of the second electrode layer 200 of FIG. 6.

Referring to FIGS. 1, 6, and 7, the second electrode layer 200 according to one or more embodiments is provided on another surface of the intermediate layer 300 to face the first electrode layer 100. The second electrode layer 200 includes a portion to be inserted into the living body and a portion connected to an external electronic device to correspond to the shapes of the probe unit 10 and the pad unit 20 of the implantable biosensor 1 described above. The second electrode layer 200 may include a second electrode 210, a second coupling layer 220, and a second protective layer 230.

The second electrode 210 is a reference electrode for accurately measuring a voltage at the first electrode 110. For example, the second electrode 210 may be a reference electrode of a three electrode system. In addition, the second electrode 210 measures a potential difference with the first electrode 110 and, since the second electrode 210 is connected to a voltmeter and the resistance thereof is very large, no current may flow in the second electrode 210. By including the second electrode 210, it is possible to prevent a potential applied to the first electrode 110 from being disturbed by a reaction with a bio material. The second electrode 210 may include a second electrode end 211, a second leading wire 212, and a second pad 213.

The second electrode end 211 is located at the leading end of the second electrode 210 in one direction (e.g., the X-axis direction of FIG. 2). The second electrode end 211 may be located in the sensor 11 of the probe unit 10 and may be inserted into the living body. The shape of the second electrode end 211 is not particularly limited, and, in one or more embodiments, the leading end portion of the second electrode end 211 may have the shape of a flat plate convex in one direction. The size of the second electrode end 211 is not particularly limited and may correspond to the size of a metal paste 240 described below.

The second leading wire 212 extends in one direction from the second electrode end 211 and physically and electrically connects the second pad 213 described below and the second electrode end 211. The second leading wire 212 be located in the connector 12 of the probe unit 10 and may be inserted into the living body. The second leading wire 212 may have the shape of a ribbon that is curved in the lengthwise direction. Therefore, even when the implantable biosensor 1 is contracted, extended, or bent in the lengthwise direction while being inserted into the living body, deformation or damage of the entire implantable biosensor 1 may be minimized. Also, even when the implantable biosensor 1 collides with a living tissue during the process of being inserted into the living body, the impact applied to the implantable biosensor 1 may be reduced. Also, the elasticity of the implantable biosensor 1 in the lengthwise direction may be further improved.

The second pad 213 extends rearward from the second leading wire 212. The second pad 213 may be located in the pad unit 20 and may be connected to an external electronic device. The size and the shape of the second pad 213 are not particularly limited, but the second pad 213 may have an area larger than the second electrode end 211 and the second leading wire 212. In one or more embodiments, the second pad 213 may have the shape of a flat plate narrowed toward the second leading wire 212.

The second electrode end 211, the second leading wire 212, and the second pad 213 may all be arranged on the same plane. Also, the second electrode end 211, the second leading wire 212, and the second pad 213 may all include Au. However, one or more embodiments are not limited thereto, and a different material may be partially employed in consideration of a bio material to be measured.

Also, the second electrode 210 is a thin-film type electrodes exhibiting excellent elasticity and flexibility, and thus the second electrode 210 and the auxiliary electrode 120 may be naturally curved as forces are applied in three-axis directions.

Referring to FIGS. 6 and 7, the second electrode layer 200 may further include a second coupling layer 220. The second coupling layer 220 is provided on one surface of the second electrode layer 200. For example, as shown in FIG. 1, the second coupling layer 220 may be provided on the bottom surface of the intermediate layer 300 described below and may couple the second electrode layer 200 with the intermediate layer 300. The size and the shape of the second coupling layer 220 may correspond to the size and the shape of the second electrode 210. The material constituting the second coupling layer 220 is not particularly limited, and, in one or more embodiments, the material constituting the second coupling layer 220 may be $SiO_2$. Also, the second coupling layer 220 may have a shape corresponding to the shapes of the probe unit 10 and the pad unit 20 described above.

Also, referring to FIGS. 6 and 7, the second electrode layer 200 may further include a second protective layer 230. The second protective layer 230 may be provided on one surface of the second coupling layer 220 to cover the second electrode 210. The material constituting the second protective layer 230 is not particularly limited, and, in one or more embodiments, the material constituting the second protective layer 230 may be PDMS or PI.

The second protective layer 230 may include a protective layer 2a 231 covering the top surface (see FIG. 1) of the second electrode 210 and a protective layer 2b 232 covering the bottom surface of the second electrode 210. The protective layer 2a 231 is provided on the bottom surface of the second coupling layer 220 and has a shape and a size similar to those of the second coupling layer 220. The protective layer 2b 232 is provided on the bottom surface of the second electrode 210 and is partially cut. In detail, portions of the protective layer 2b 232 corresponding to the second electrode end 211 and the second pad 213 may be cut. Therefore, one surface of each of the second electrode end 211 and the second pad 213 may be exposed. Also, the second pad 213 may be connected to an external electronic device. Also, the second leading wire 212 may be covered by the second protective layer 230.

According to the configuration as described above, the second electrode 210 is entirely covered by the second protective layer 230, thereby reducing the impact applied to the implantable biosensor 1 when the implantable biosensor 1 is inserted into the living body. Also, the overall elasticity and flexibility of the implantable biosensor 1 may be further improved.

In one or more embodiments, the first protective layer 150 and the second protective layer 230 may constitute an integral protective layer. In other words, the first protective layer 150 and the second protective layer 230 may constitute an integral protective layer that entirely covers the first electrode layer 100, the second electrode layer 200, and the intermediate layer 300 instead of being physically separated from each other. Therefore, the implantable biosensor 1 may be more firmly protected from external impact or permeation of foreign substances, and the overall elasticity and flexibility thereof may be further improved.

Referring to FIGS. 6 and 7, the second electrode layer 200 may further include the metal paste 240. The metal paste 240 may be provided on one surface of the second electrode end 211. Therefore, the reference of a potential applied to the first electrode 110 may be more surely maintained. The size and the shape of the metal paste 240 may correspond to the size and the shape of the exposed second electrode end 211. Also, a material constituting the metal paste 240 is not particularly limited, and, in one or more embodiments, the metal paste 240 may include silver-silver chloride (Ag—AgCl).

Figure 8:
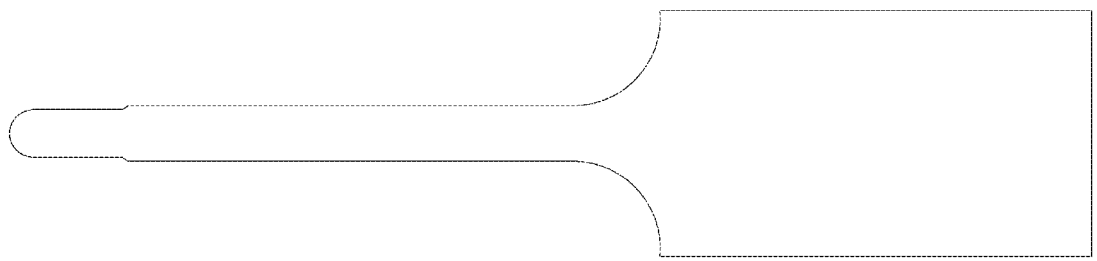
FIG. 8 is a plan view of an intermediate layer of FIG. 1.

Referring to FIGS. 1 and 8, the implantable biosensor 1 according to one or more embodiments may further include the intermediate layer 300. The intermediate layer 300 is interposed between the first electrode layer 100 and the second electrode layer 200. The size and the shape of the intermediate layer 300 may correspond to the sizes and the shapes of the first electrode layer 100 and the second electrode layer 200. The material constituting the intermediate layer 300 is not particularly limited and may be an elastomer. In one or more embodiments, the intermediate layer 300 may include PDMS. Also, the intermediate layer 300 is a thin film-type substrate with excellent elasticity and flexibility, and thus the intermediate layer 300 may be naturally curved as forces in three-axis directions are applied thereto.

Next, referring to FIGS. 1 to 8, a method of manufacturing the implantable biosensor 1 according to another embodiment will be described.

<Formation of First Electrode Layer 100>

First, a sacrificial layer is provided on a glass substrate, and then the first protective layer 150 (protective layer 1a 151) is coated thereon. However, it is not necessary to coat the first protective layer 150, and the first protective layer 150 may be omitted. Hereinafter, for convenience of explanation, it will be described that the first protective layer 150 is included. The first protective layer 150 may include PDMS or PI.

Next, an electrode pattern is formed on the top surface of the first protective layer 150. In detail, the first electrode 110 and the auxiliary electrode 120 are arranged on the top surface of the first protective layer 150, and then the fixing material 133 is grown on the top surface of the first electrode end 111 of the first electrode 110. Here, the fixing material 133 may be zinc oxide nano-rods grown on the top surface of the first electrode end 111.

Next, the first protective layer 150 (protective layer 1b 152) is coated once more to entirely cover the first electrode 110, the auxiliary electrode 120, and the fixing material 133. In other words, the first electrode 110, the auxiliary electrode 120, and the fixing material 133 are encapsulated in the first protective layer 150.

Next, portions of the top surface of the first protective layer 150 corresponding to the first electrode 110 and the auxiliary electrode 120 are etched. In detail, portions of the top surface of the first protective layer 150 corresponding to the first electrode end 111 having provided thereon the fixing material 133, the auxiliary electrode end 121, the first pad 113, and the auxiliary pad 123 are etched to expose.

Next, the support ring 132 is provided on the exposed top surface of the first electrode end 111, and more particularly, the portion on which the fixing material 133 is provided. Here, the support ring 132 may be provided, such that the fixing material 133 is included in the internal space of the support ring 132.

<Formation of Second Electrode Layer 200>

First, a sacrificial layer is provided on a glass substrate, and then the second protective layer 230 (protective layer 2a 231) is coated thereon. However, it is not necessary to coat the second protective layer 230, and the second protective layer 230 may be omitted. Hereinafter, for convenience of explanation, it will be described that the second protective layer 230 is included. The second protective layer 230 may include PDMS or PI.

Next, an electrode pattern is formed on the top surface of the second protective layer 230. Next, the second electrode 210 is formed on the top surface of the second protective layer 230.

Next, the second protective layer 230 (protective layer 2b 232) is coated once more to entirely cover the second electrode 210. In other words, the second electrode 210 is encapsulated in the second protective layer 230.

Next, a portion of the top surface of the second protective layer 230 corresponding to the second electrode 210 is etched. In detail, portions of the second protective layer 230 corresponding to the second electrode end 211 and the second pad 213 are etched to expose.

<Formation of Intermediate Layer 300>

First, a photoresist is coated on a wafer. Here, the wafer may be a silicon wafer. Also, the photoresist may be SU-8.

Next, patterning is performed to correspond to the shape of the intermediate layer 300, thereby forming a mold. Next, a curing liquid is injected into the mold and cured. Here, the curing liquid may be PI. Next, the cured PI is retrieved from the mold to form the intermediate layer 300.

<Surface Treatment and Manufacturing of Implantable Biosensor 1>

First, the first electrode layer 100 and the second electrode layer 200 fabricated as described above are transferred to a transfer body. As the sacrificial layers are removed during a transfer process, the first electrode layer 100 and the second electrode layer 200 are separated from the glass substrate.

Next, the first coupling layer 140 is provided on one surface of the first electrode layer 100, and the second coupling layer 220 is provided on one surface of the second electrode layer 200.

Next, surface treatment is performed on the first coupling layer 140 and the second coupling layer 220. The surface treatment is a process for bonding the first coupling layer 140, the second coupling layer 220, and the intermediate layer 300 to one another. The surface treatment is not particularly limited, and oxygen plasma treatment may be performed.

Next, the first coupling layer 140 is provided on one surface of the intermediate layer 300, and the second coupling layer 220 is provided on the other surface of the intermediate layer 300.

Next, the sensing material 131 is provided on the first electrode layer 100, and the metal paste 240 is provided on the second electrode layer 200. In detail, the sensing material 131 is provided in the internal space of the support ring 132 provided at the first electrode end 111 of the first electrode layer 100. Therefore, the fixing material 133 provided in the internal space of the support ring 132 fixes the sensing material 131. Also, in case of using an enzyme as the sensing material 131, the enzyme mixed with a solvent is provided in the internal space of the first support ring 132 and is dried to remove the solvent. The enzyme without the solvent may have a convex shape that protrudes upwardly due to surface tension. Also, the metal paste 240 is applied on the second electrode end 211 of the second electrode 210. Therefore, the implantable biosensor 1 may be finally manufactured.

Next, a method of sensing and measuring a bio material by using the implantable biosensor 1 according to one or more embodiments will be described.

First, the probe unit 10 of the implantable biosensor 1 is inserted into the living body. Next, an external electronic device is connected to the pad unit 20. A constant potential may be applied to the first electrode 110 by using a potentiostat as an external electronic device. Also, a circuit may be formed by allowing a current to flow between the first electrode 110 and the auxiliary electrode 120. Also, by placing a voltmeter and an ammeter, an applied voltage or an applied current may be measured in real time.

In another embodiment, a potential applied to the first electrode 110 may be equal to one of voltages that may be applied by using a potentiostat. For example, in the implantable biosensor 1 according to one or more embodiments, when a target material to be measured is dopamine, the dopamine may be oxidized to DA quinone by using tyrosinase as the sensing material 131 and a reduction current generated during a process that the DA quinone is reduced back to dopamine may be measured, thereby measuring the concentration of the dopamine. Here, the cyclic voltammetry may be used to select a voltage having excellent measurement accuracy of a reduction current, that is, a voltage that is most sensitive to charges generated or consumed through a redox reaction of dopamine and DA quinone.

Next, a constant voltage is applied to the implantable biosensor 1 by using an external electronic device. For example, a voltage that the implantable biosensor 1 reacts most sensitively may be applied by using the above-described cyclic voltammetry.

Therefore, a bio material causes an oxidation reaction or a reduction reaction with the sensing material 131, and charges are generated or consumed as the bio material is oxidized or reduced again at the first electrode 110. By sensing charges generated during the process and measuring a current value, the bio material may be sensed and the concentration thereof may be measured. In detail, when a bio material to be measured is dopamine, the dopamine reacts with an enzyme (i.e., tyrosinase), which is a sensing material 131 inserted into the living body. Dopamine oxidized by tyrosinase is present in the form of DA quinone, which is reduced again at the first electrode 110. By measuring a current generated during the process, the concentration of the dopamine may be measured.

In the implantable biosensor 1 according to one or more embodiments, around the intermediate layer 300, the first electrode layer 100 is provided on one surface of the implantable biosensor 1, and the second electrode layer 200 is provided on the other surface of the implantable biosensor 1. In other words, by forming electrode layers on both surfaces, an overall sensor may be miniaturized. Accordingly, unlike a biosensor of a conventional three-electrode system, in which a working electrode, a counter electrode, and a reference electrode need to be provided separately, three electrodes are integrated in one sensor, thereby reducing the size of the sensor. As a result, the feeling of irritation and damages to the interior of the living body may be minimized when the sensor is inserted into the living body.

Also, in the implantable biosensor 1 according to one or more embodiments, the first electrode layer 100, the second electrode layer 200, and the intermediate layer 300, which are thin film-type layers, are stacked, and thus the implantable biosensor 1 exhibits excellent elasticity and flexibility. Also, since the first leading wire 112 and the auxiliary leading wire 122 of the first electrode layer 100 and the second leading wire 212 of the second electrode layer 200 have ribbon-like shape curved in the lengthwise direction, the implantable biosensor 1 exhibits more excellent elasticity in the lengthwise direction.

Also, the implantable biosensor 1 according to one or more embodiments is entirely covered by the first protective layer 150 and the second protective layer 230. Therefore, structural stability of the implantable biosensor 1 may be secured and the implantable biosensor 1 may be protected by absorbing impact occurring while the implantable biosensor 1 is being inserted into the living body. Also, by forming the first protective layer 150 and the second protective layer 230 with an elastomer, elasticity and flexibility of the implantable biosensor 1 may be secured.

Also, in the implantable biosensor 1 according to one or more embodiments, the sensing unit 130 may be provided on one side of the first electrode end 111 to be inserted into the living body, thereby accurately sensing a bio material. Also, by including the sensing material 131 that selectively reacts with a bio material and the support ring 132 and the fixing material 133 for fixing the sensing material 131, the bio material may be sensed more stably.

Also, the implantable biosensor 1 according to one or more embodiments includes a portion to be inserted into the living body in the form of a probe, thereby reducing the feeling of irritation and damages to the interior of the living body while the implantable biosensor 1 is being inserted into the living body.

In an implantable biosensor according one or more embodiments, electrodes may be arranged on both surfaces, thereby reducing the overall size of the implantable biosensor and minimizing the feeling of irritation and damages to the interior of the living body while the implantable biosensor is being inserted into the living body. Also, in the implantable biosensor according to one or more embodiments, thin film-members layers are stacked, and thus the implantable biosensor exhibits excellent elasticity and flexibility. Also, the implantable biosensor according to one or more embodiments is entirely covered by protective layers, thereby ensuring structural stability and absorbing impact occurring while the implantable biosensor is being inserted into the living body. Also, the implantable biosensor according to one or more embodiments may sense a bio material stably and precisely by using a sensing unit that selectively reacts with the bio material. Also, the implantable biosensor according to one or more embodiments includes a portion to be inserted into the living body in the form of a probe, thereby reducing the feeling of irritation and damages to the interior of the living body while the implantable biosensor is being inserted into the living body.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An implantable biosensor comprising:
   an intermediate layer;
   a first electrode layer provided on one surface of the intermediate layer and comprising a first electrode configured to react with a bio material and an auxiliary electrode electrically connected to the first electrode; and
   a second electrode layer provided on another surface of the intermediate layer to face the first electrode layer and comprising a second electrode operating as a reference electrode,
   wherein the first electrode comprises:
   a first electrode end provided at a leading end;
   a first leading wire extending from the first electrode end and having an elongated band shape with two side edges, wherein the two side edges of the first leading wire progress with meandering in a first direction, and the first leading wire is stretchable in the first direction; and a first pad connected to the first leading wire and configured to be connected to an outside, wherein the auxiliary electrode comprises:

an auxiliary electrode end provided at a leading end;

an auxiliary leading wire extending from the auxiliary electrode end and having an elongated band shape with two side edges, wherein the two side edges of the auxiliary leading wire progress with meandering in the first direction, and the auxiliary leading wire is stretchable in the first direction; and an auxiliary pad connected to the auxiliary leading wire and configured to be connected to an outside, wherein the second electrode comprises:

a second electrode end provided at a leading end; and a second leading wire extending from the second electrode end and having an elongated band shape with two side edges, wherein the two side edges of the second leading wire progress with meandering in the first direction, and the second leading wire is stretchable in the first direction; and a second pad connected to the second leading wire and configured to be connected to an outside.

2. The implantable biosensor of claim 1, wherein the first electrode further comprises a sensing unit provided at a leading end of the first electrode and configured to sense the bio material.

3. The implantable biosensor of claim 2, wherein the sensing unit comprises:

a support ring having an annular shape, provided on one surface of the first electrode, and having an internal space;

a fixing material provided in the internal space of the support ring; and a sensing material provided on a top surface of the fixing material and reacting with the bio material.

4. The implantable biosensor of claim 3, wherein the sensing material is an enzyme, and an isoelectric point of the fixing material is higher than an isoelectric point of the sensing material.

5. The implantable biosensor of claim 4, wherein the fixing material is zinc oxide nano-rods, and the sensing material is tyrosinase.

6. The implantable biosensor of claim 1, wherein the second electrode further comprises a metal paste provided on one side thereof.

7. The implantable biosensor of claim 1, further comprising a protective layer entirely covering the intermediate layer, the first electrode layer, and the second electrode layer, wherein the intermediate layer and the protective layer each comprise a flexible biocompatible polymer.

* * * * *